United States Patent [19]

Melzig et al.

[11] Patent Number: 5,645,768
[45] Date of Patent: Jul. 8, 1997

[54] PHOTOCHROMIC COMPOUNDS

[75] Inventors: Manfred Melzig, Wessling; Herbert Zinner, Pentling, both of Germany

[73] Assignee: Optische Werke G. Rodenstock, Munich, Germany

[21] Appl. No.: 580,298

[22] Filed: Dec. 28, 1995

Related U.S. Application Data

[63] Continuation-in-part of Ser. No. 392,969, Feb. 28, 1995, abandoned.

[30] Foreign Application Priority Data

Jun. 28, 1993 [DE] Germany ............................ 43 21 485.1

[51] Int. Cl.⁶ .............................. G02B 5/23; C07D 311/82
[52] U.S. Cl. ........................ 252/586; 549/24; 549/25; 549/26; 549/27; 549/223; 548/131; 548/143
[58] Field of Search ............................ 252/586; 549/24, 549/25, 26, 27, 223, 331, 344; 548/131, 143

*Primary Examiner*—Amelia Owens
*Attorney, Agent, or Firm*—Antonelli, Terry, Stout & Kraus, LLP

[57] ABSTRACT

A photochromic compound, in particular, for tinting optical elements made of a plastic material has reduced mobility in plastic material. The photochromic compound is a photochromic 2H-pyran and is distinguished by the aromatic residues being chemically rigidly attached in the 2-position to a spiropyran.

4 Claims, No Drawings

PHOTOCHROMIC COMPOUNDS

This application is a Continuation-in-Part application of application Ser. No. 08/392,969 filed Feb. 28, 1995, now abandoned.

TECHNICAL FIELD

The present invention relates to photochromic compounds, in particular, for tinting optical elements made of a plastic material.

STATE OF THE ART

Photochromic compounds of this type are, by way of illustration, pyrans, a long-known and well-examined class of photochromic dyes. Thus, the diphenylnaphthopyrans described in U.S. Pat. No. 5,066,818 or U.S. Pat. No. 4,818,096 have, by way of illustration, quite good application properties.

The molecule described in these printed publications, however, possess high mobility in various plastic materials, in particular, at raised temperatures like those, by way of illustration, occurring tinting and antireflection coating processes. This mobility presents problems, by way of illustration, when ophthalmic lenses or other objects that are to be photochromically tinted are tinted using both pyrans and photochromic spironaphthoxazins in order to produce neutral brown or gray tinting (cf. also EP-A-0 397 803).

When used in combination for tinting, the pyrans migrate from the surface substantially faster and, therefore, deeper into the polymer than the oxazins. There they are impinged with substantially less UV-irradiation than the oxazins closer to the surface, because the latter largely already absorb the UV-radiation. For this reason, tinting using pyrans is substantially less with regard to the amounts utilized than tinting using oxazins so that obtaining neutral brown or gray tinting is difficult.

On the other hand, in antireflection coating, which usually is conducted at a substrate temperature of more than 80° C., the pyrans migrate substantially faster to the surface than the oxazins and cause the layers to separate.

Although the adamantanospiropyrans also described in U.S. Pat. No. 4,818,096 possess less mobility than diphenylnaphthopyrans, the rate at which they become lighter is too slow. Moreover, these dyes only provide yellow tones.

DESCRIPTION OF THE INVENTION

The object of the present is to provide photochromic compounds which possess the good properties, by way of illustration, of the diphenylnaphthopyrans described in U.S. Pat. No. 5,066,818 while possessing distinctly reduced mobility in plastic materials, in particular used for ophthalmic lenses.

A solution to this object in accordance with the present invention is to provide a photochromic compound, in particular, for tinting optical elements made of a plastic material, characterized by in a photochromic 2H-pyran, the aromatic residues being chemically rigidly attached in the 2-position to a spiropyran. Further embodiments of the present invention are the subject-matter of the following description.

An element of the present invention is that with a photochromic 2H-pyran, the aromatic residues attach in the 2-position chemically rigidly to a spiropyran. Due to the rigid linkage, by way of illustration, of both phenyl rings, which in the case of the molecules described in U.S. Pat. No. 5,066,618 are feebly mobile in relation to each other, the diffusion velocity of the molecules is drastically reduced.

Linkage may occur in various different ways, by way of illustration, in such a manner that the compounds resulting from the linkage are fluorene, dibenzosuberone, anthrone, xanthene or thioxanthen. The structural formula of the compounds known from U.S. Pat. No. 5,066,818 is shown below if linkage occurs via —CO— to anthrone. An exemplary structural formula is given in the following:

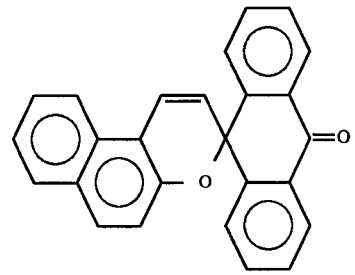

Alternatively, linkage may be produced via 1 to 3 $CH_2$ bridges. The photochromic pyran may be a diphenyl (naphtho)pyran or a substituted dinaphthyl or phenylnaphthyl derivative. The same effect occurs if the substituent, by way of illustration acetoxy- or benzoyloxy-, in the 3-position of the naphthalene system is substituted by the oxadiazol group described in DE-A-38 14 631.

If the production of photochromic compounds is based on dihydroxy compounds of naphthalene, phenanthrene, etc., dispiropyrans are yielded. These are, due to their considerably larger steric requirements, also less migration prone.

Moreover, photochromic molecules bearing two (or more) photochromic subsystems which react differently in color and kinetics can be synthesized by replacing hydroxyl groups in non-equivalent positions, by way of illustration in 1,6 or 1,3-dihydroxynaphthaline with an acetylide or replacing various acetylides as is described in a patent application that was filed by the applicant on the same day. Several or all the described solution methods of realizing a compound by, by way of illustration, converting 3,8-dihydroxynaphthoic-(2)-acid to a corresponding 2-diazol derivative and replacing the latter first in the 8-position with an anthrol acetylide and then in the 3-position with a fluorenol acetylide.

The photochromic compounds used in the present invention have the formula:

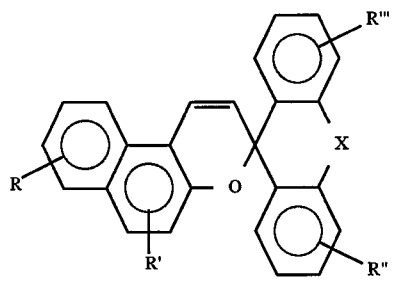

wherein

R is H, —OH, $C_1$–$C_{10}$ alkyl, $C_5$–$C_7$ cycloalkyl, phenyl, mono-or disubstituted phenyl, $C_1$–$C_4$ alkoxy, halogen, acrylyl, methacrylyl, acryloxy($C_1$–$C_4$)alkyl, methacryloxy($C_1$–$C_4$)alkyl, five or six-membered heterocyclic groups connected to the naphthopyran rings by a single bond, e.g. furyl, thienyl or oxadiazole, preferably in the 3 position.

R' is H, —OH, $C_1$–$C_{10}$ alkyl, $C_5$–$C_7$ cycloalkyl, phenyl, mono-or disubstituted phenyl, $C_1$–$C_4$ alkoxy, halogen, acrylyl, methacrylyl, acryloxy($C_1$–$C_4$)alkyl, methacryloxy($C_1$–$C_4$)alkyl, five or six-membered heterocyclic groups connected to the naphthopyran rings by a single bond, e.g. furyl, thienyl or oxadiazol, preferably in the 3 position.

R" is H, —OCOCH$_3$, a fused benzo, or a fused naphthyl;

R'" is H, —CH$_3$, —OCOC$_6$H$_5$, a fused benzo, or a fused naphthyl; and

X is —CO—, —CH$_2$—CO—, —CH$_2$—CH$_2$—CH$_2$— S, O, —CH$_2$—CH$_2$—, —CH$_2$— or a single bond.

The more preferred compounds according to the present invention have the formula:

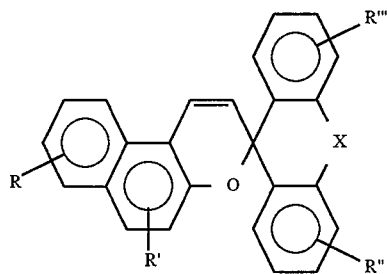

wherein

R is H or OCH$_3$;

R' is H, OCH$_3$, Br or OCOCH$_3$;

R" is H;

R'" is H, CH$_3$, OCOC$_6$H$_5$ or 2,3-benzo; and

X is S, O, —CH$_2$—CH$_2$—, —CH$_2$— or a single bond.

A photochromic composition comprising an optical plastic material and the photochromic compounds represented in the formulas above are also part of the present invention.

As measurement of the actual diffusion velocity of photochromic organic molecules in plastic materials is exceptionally expensive and complicated, an indirect method of determination is selected. Under the influence of heat, inverse migration of the photochromic molecules in a tinted ophthalmic lens, by way of illustration, made of polydiethyleneglycolbisallylcarbonate (trade name CR 39) according to DE 3345 639, occurs toward the surface. This heat effect is, by way of illustration, in the antireflection coating of such ophthalmic lenses unavoidable and also occurs in ordinary use of glasses, e.g., in a glove compartment of an automobile in summer. The inversely migrating photochromic molecules impair the interface of the plastic material/ antireflection coating, be it due to signs of separation in the layer or due to agglomeration of the dye. The latter is visible to the naked eye as spot formation activated by light.

EXAMPLE 1 a) Production of carbinol:

39.6 g (0.22 mol) of 9-fluorenon are dissolved in 120 ml of dry dimethyl sulfoxide; 20.3 g (0.22 mol) of lithium acetylide ethylene diamine complex are added dropwise to this neon-yellow solution while stirring. The solution gradually turns dark yellow. The mixture continues to the stirred for 16 hours at 25° C. and then is poured onto 400 g of crushed ice and made acidic with diluted HCl. The yellowish white precipitation formed upon introducing the solution into the ice becomes lumpy with neutralization. The suspension is extracted with ether until the precipitation depositing at the phase interface is completely dissolved in the ether. The unified ether extracts are dried and filtered using Na$_2$SO$_4$. The ether is withdrawn from the filtrate in a rotary evaporator. 21 g of a yellow oil is left which is pure enough for further processing.

b) Conversion to a pyran:

First the product obtained under a) is stirred with 20 g (0.1 mol) of 3-acetyl-2-naphthol in 1600 ml of toluol at room temperature for 8 hours and then boiled for 2 hours under reflux. The still warm solution is freed of the still present starting product by means of extraction using a Na$_2$SO$_3$ solution. The organic phase is dried using Na$_2$SO$_4$, filtered, reduced to approximately 70 ml and chromatographed with toluol on Al$_2$O$_3$. The running yellow fraction is rejected, the subsequent red-orange photochromic fraction is collected and is reduced for drying. The obtained product is recrystallized out of ether/hexane. The obtained substance is identified as spiro(fluorene-9.2'-(2H)-naphtho(2.3-b)pyran) by means of a NMR spectrum.

The production of examples 2–12 occurs in an analogous manner using the appropriate ketones, respectively substituted naphtholenes as starting compounds. The 5 reference examples are synthesized according to the original specifications in the patent publications.

c) Tinting:

With the compounds according to the present invention as well as comparable substances according to the state of the art, commercially available zero-power lenses made of polydiethyleneglycolbisallyl carbonate (*71 mm, center thickness approximately 2 mm) are tinted photochromatically on the convex side in a known manner (DE 33 45 639) using lacquer techniques. The dye concentration amounts to 4% inn the spray-ready lacquer, tinting is conducted for 90 minutes at 160° C. 10 lenses are provided with a wideband antireflection coating, 10 others with first an organic hard layer of a polysiloxane basis and then a super antireflection coating with a clean-effect. These test lenses were exposed to a temperature of 65° C. for 6 hours and then optically evaluated. If there are no defects, the test is repeated up to a maximum of 5 times. The results are shown in tables 2 and 3.

TABLE 1

Substitution scheme of the invented photochromic compounds, respectively those according to the state of the art

| Example | R | R' | R" | R'" | X |
|---|---|---|---|---|---|
| 1 | H | OCOCH$_3$ | H | H | — |
| 2 | H | H | H | H | — |
| 3 | H | H | H | H | CH$_2$ |
| 4 | H | H | H | H | CH$_2$—CH$_2$ |
| 5 | H | H | H | H | O |
| 6 | H | H | H | H | S |
| 7 | H | H | H | 2,3-benzo | — |
| 8 | OCH$_3$ | H | H | H | — |
| 9 | H | OCH$_3$ | H | H | — |
| 10 | H | H | H | 1-CH$_3$ | — |
| 11 | H | Br | H | H | — |
| 12 | H | H | H | OCOC$_6$H$_5$ | — |

Comparison (all the examples have above X not linked, thus free aryl residues)

TABLE 1-continued

| Example | R | R' | R" | R'" | |
|---------|-----|------|--------|-------|---------------------|
| 1 | H | H | H | H | U.S. Pat. No. 3,567,605 |
| 2 | OCH₃ | H | H | H | |
| 3 | H | OCH₃ | H | H | U.S. Pat. No. 5,238,981 |
| 4 | H | H | OCOCH₃ | H | WO 92/09593 |
| 5 | H | H | H | 2-CH₃ | U.S. Pat. No. 5,066,818 |

TABLE 2

Behavior using wideband antireflection coating; failure in the xth cycle

| Example x = | 1 | 2 | 3 | 4 | 5 |
|-------------|---|-----|------|------|-------|
| 1 | — | — | — | 1s | 2s |
| 2 | — | — | 1s | — | 1s |
| 3 | — | — | 2s | 2s | 1s/1f |
| 4 | — | 1s | 2s | 2s | 3s |
| 5 | — | — | 1s | 1s | 2s/1f |
| 6 | — | — | 1s | 2s | 1s |
| 8 | — | — | — | 2s | 1s |
| 10 | — | — | — | 1s | 1s/1f |
| 12 | — | — | — | — | 2s |
| Comparison | | | | | |
| 1 | — | 2s/2f | 1s/4f | 1s | |
| 2 | 1s | 5s/1f | 2f | 1f | |
| 3 | — | 4s/2f | 2s/2f | | |

TABLE 3

Behavior with a hard layer and super-wideband antireflection coating.

| Example x = | 1 | 2 | 3 | 4 | 5 |
|-------------|---|----|----|------|-------|
| 1 | — | — | — | 1s | 1s |
| 2 | — | — | 1s | 2s | 1s |
| 3 | — | — | 3s | 2s | 1s |
| 4 | — | 1s | — | 2s/1f | 3s |
| 5 | — | — | 2s | 4s/1f | 2s |
| 7 | — | — | — | — | — |
| 9 | — | — | 1s | 3s | 3s |
| 11 | — | — | 1s | 1s | 2s/1f |
| Comparison | | | | | |
| 4 | — | 2s/3f | 3s/1f | 1s | |
| 5 | — | 4s | 6s | | |

Evaluation: s = layer separation, f = spottiness If both defects occurred in a lens in a control, only spottiness was evaluated.

What is claimed is:

1. A photochromic compound having the formula:

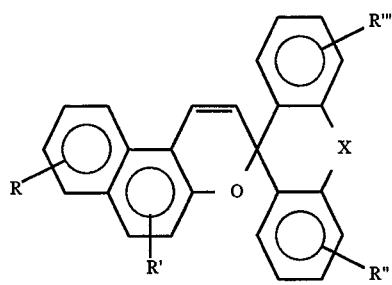

wherein
R is H or OCH₃;
R' is H, OCH₃, Br or OCOCH₃;
R" is H;
R'" is H, CH₃, OCOC₆H₅ or 2,3-benzo; and
X is S, O, —CH₂—CH₂—, —CH₂— or a single bond.

2. A photochromic compound having the formula:

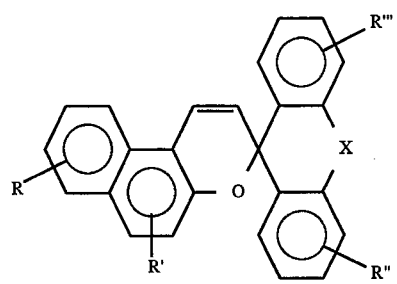

wherein
R is H, —OH, C₁-C₁₀ alkyl, C₅-C₇ cycloalkyl, phenyl, mono-or disubstituted phenyl, C₁-C₄ alkoxy, halogen, acrylyl, methacrylyl, acryloxy C₁-C₄ alkyl, methacryloxy C₁-C₄ alkyl, furyl, thienyl or oxadiazole,
R' is H, —OH, C₁-C₁₀ alkyl, C₅-C₇ cycloalkyl, phenyl, mono-or disubstituted phenyl, C₁-C₄ alkoxy, halogen, acrylyl, methacrylyl, acryloxy C₁-C₄ alkyl, methacryloxy C₁-C₄ alkyl, furyl, thienyl or oxadiazole,
R" is H, —OCOCH₃, a fused benzo, or a fused naphthyl;
R'" is H, —CH₃, —OCOC₆H₅, a fused benzo, or a fused naphthyl; and
X is —CO—, —CH₂—CO—, —CH₂—CH₂—CH₂—, S, O, —CH₂—CH₂—, —CH₂— or a single bond.

3. A photochromic composition comprising an optical plastic material and a photochromic compound of claim 1.

4. A photochromic composition comprising an optical plastic material and a photochromic compound of claim 2.

* * * * *